United States Patent
Fredriksson et al.

(10) Patent No.: US 12,179,038 B2
(45) Date of Patent: Dec. 31, 2024

(54) METHOD, A COMPUTER PROGRAM AND A COMPUTER SYSTEM FOR OPTIMIZATION OF AT LEAST ONE TREATMENT PLAN

(71) Applicant: RaySearch Laboratories AB, Stockholm (SE)

(72) Inventors: Albin Fredriksson, Stockholm (SE); Rasmus Bokrantz, Stockholm (SE); Erik Engwall, Hägersten (SE); Kjell Eriksson, Bålsta (SE); Lars Glimelius, Stockholm (SE)

(73) Assignee: RaySearch Laboratories AB, Stockholm (SE)

( * ) Notice: Subject to any disclaimer, the term of this patent is extended or adjusted under 35 U.S.C. 154(b) by 768 days.

(21) Appl. No.: 17/415,768

(22) PCT Filed: Dec. 12, 2019

(86) PCT No.: PCT/EP2019/084811
§ 371 (c)(1),
(2) Date: Jun. 18, 2021

(87) PCT Pub. No.: WO2020/126790
PCT Pub. Date: Jun. 25, 2020

(65) Prior Publication Data
US 2022/0072334 A1    Mar. 10, 2022

(30) Foreign Application Priority Data
Dec. 20, 2018 (EP) .................................. 18214611

(51) Int. Cl.
*A61N 5/10* (2006.01)
(52) U.S. Cl.
CPC .... *A61N 5/1031* (2013.01); *A61N 2005/1087* (2013.01)

(58) Field of Classification Search
CPC .................................................... A61N 5/1031
USPC ........................................................ 607/88
See application file for complete search history.

(56) References Cited

U.S. PATENT DOCUMENTS

| | | |
|---|---|---|
| 2009/0089092 A1 | 4/2009 | Johnson et al. |
| 2013/0090549 A1 | 4/2013 | Meltsner et al. |
| 2016/0144198 A1* | 5/2016 | Löf .................. G16H 40/20 600/1 |

FOREIGN PATENT DOCUMENTS

| | | |
|---|---|---|
| EP | 2 999 517 A1 | 3/2016 |
| JP | 2018-510664 A | 4/2018 |
| WO | WO-2015/090457 A1 | 6/2015 |

OTHER PUBLICATIONS

Unkelbach, Jan et al., "Optimization of combined proton-photon treatments," *Radiotherapy and Oncology* 128, pp. 133-138, 2018.

* cited by examiner

*Primary Examiner* — Nadia A Mahmood
(74) *Attorney, Agent, or Firm* — Faegre Drinker Biddle & Reath LLP

(57) ABSTRACT

A method of optimizing the use of resources in treatment planning involving more than one radiation set delivered to one or more patients, the radiation sets requiring different resources, respectively, wherein the optimization is performed using an optimization problem comprising an optimization function related to the first and second sets of resources. The method may be used for optimizing one plan for one patient, or a number of plans for different patients, in such a way that the available resources are used in the best possible way.

11 Claims, 1 Drawing Sheet

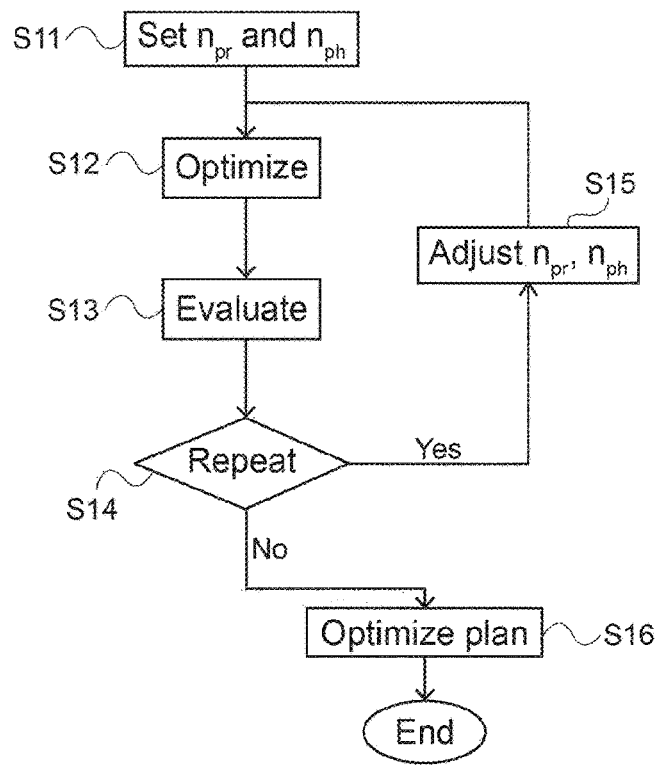
FIGURE 1
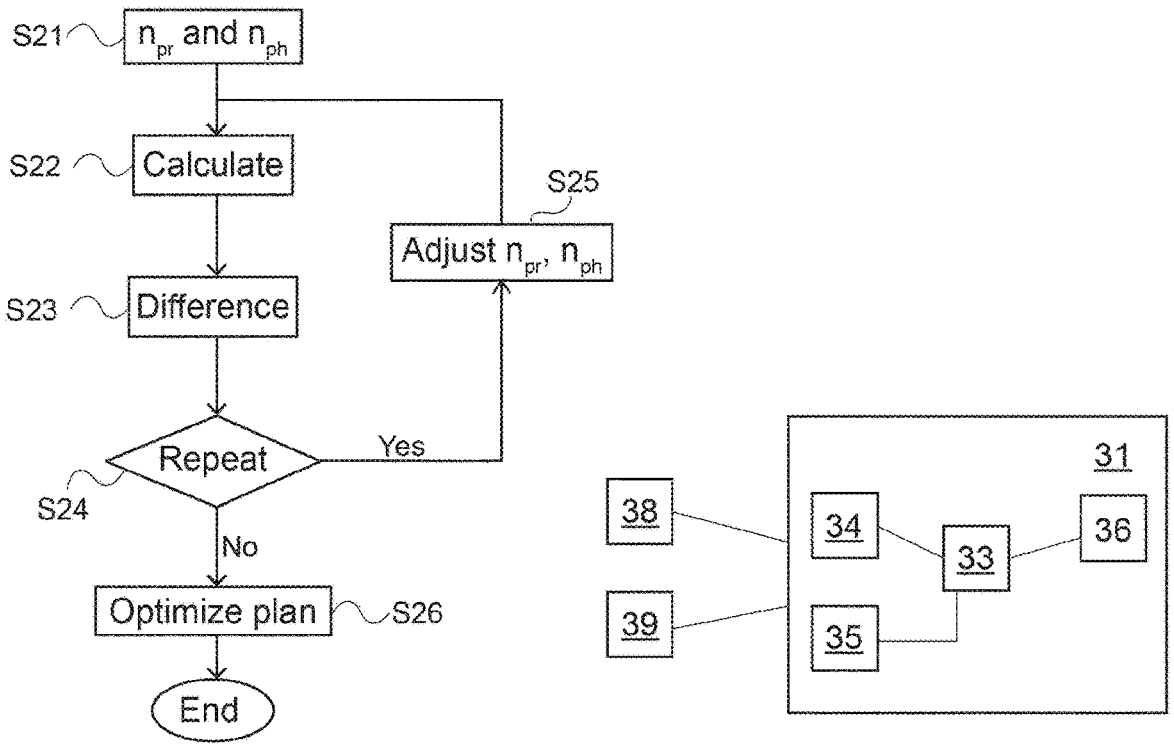
FIGURE 2
FIGURE 3

METHOD, A COMPUTER PROGRAM AND A COMPUTER SYSTEM FOR OPTIMIZATION OF AT LEAST ONE TREATMENT PLAN

This application is the National Stage of International Application No. PCT/EP2019/084811, filed Dec. 12, 2019, and claims benefit of European Patent Application No. 18214611.8, filed Dec. 20, 2018, the entire contents of which are incorporated by reference herein.

TECHNICAL FIELD

The present invention relates to a system and a method for dose planning involving several radiation sets.

BACKGROUND

In radiotherapy treatment, different types of radiation and different modalities can be used, which have different properties and involve different costs. Some modalities may be more effective than others for a particular form of treatment but may at the same time be more costly or require the use of resources that are limited.

It is a constant challenge to use the limited resources available in the best possible way, for one particular patient, and for a group of patients that need the same set of resources. One example is how to combine photon therapy and proton therapy in such a way that the resources, in particular the proton delivery system, are used in the most cost-efficient way giving the best possible result.

The most commonly used type of radiotherapy today is photon therapy, which is well established, and most facilities have resources for this. Ion therapy, typically with protons or carbon ions, enables more precise treatment and is therefore often preferable from a quality point of view. At the same time, it requires equipment that is at present much more costly and therefore more scarce. It is possible to use a combination of different types of radiation for one patient. Radiotherapy is normally delivered to the patient in a number of fractions, for example, one per day. Many patients would benefit from receiving at least some fractions as ion therapy and the rest as photon therapy. Because of the limited availability, ion therapy should be used in the cases, and to the extent, where it can provide the most positive effect.

European patent application EP2999517 discusses optimization of treatment plans for a plurality of patients by first optimizing a number of plans, possibly using different modalities, and then selecting the combination of plans that provides the best possible plan quality subject to constraints on resourced.

Unkelbach et al. Optimization of combined proton-photon treatments, *Radiother Oncol* 128(1): 133-138, 2018 discusses the optimization of dual modality treatments with the weighting between the modalities predetermined to improve upon plan quality compared to single modality treatments.

SUMMARY

It is an object of the present invention to enable the planning of radiotherapy with the most efficient use of resources possible.

The invention relates to a treatment plan optimization method for optimizing at least a first treatment plan using at least a first and a second radiation set, where the first radiation set is to be delivered to a first patient and the second radiation set is to be delivered to the first patient or to a second patient. The first and second radiation set require a first and a second set of resources, respectively, and the optimization is performed using an optimization problem comprising an optimization function related to the first and second sets of resources.

The result may be one treatment plan for one patient using at least a first and a second radiation set, a first and a second treatment plan for a first and a second patient each using one radiation set, or a first and a second treatment plan for a first and a second patient where each treatment plan may use more than one radiation set, or one treatment plan each for any number of patients, where each treatment plan uses one or more radiation sets. When planning for more than one patient, the optimization problem is designed to jointly optimize plans for multiple patients by taking into consideration the combined resource requirement and plan quality for multiple patients in the objective function and/or constraints of the optimization problem.

A radiation set is defined by the DICOM standard as a collection of radiations (for example beams in external beam radiation therapy or catheters in brachytherapy). A radiation set defines a radiotherapy treatment fraction or a part of a radiotherapy treatment fraction, which will be applied one or more times. Typically, each radiation set requires a specific set of resources for delivery of the treatment. The resources for the different radiation sets may be more or less costly and more or less available. A radiotherapy treatment is normally divided into a number of fractions, and it is possible to use different radiation sets for different fractions, for example to include more beam angles in some fractions than in others. Another common reason for using different radiation sets is when different treatment techniques or modalities are combined. The different radiation sets may be, for example, proton and photon radiation, or volumetric-modulated arc therapy (VMAT) and intensity-modulated radiation therapy (IMRT). The radiation sets may then be delivered during the same treatment fraction. These and other possible combinations will be discussed in more detail in the detailed description.

Examples of treatment techniques or modalities that may be used together include VMAT, static multi-leaf collimated IMRT (SMLC), dynamic multi-leaf collimated IMRT (DMLC), tomotherapy, active scanning of protons, helium ions, carbon ions, other ions, brachytherapy, passive scattering and uniform scanning of ions.

The method according to the invention may be used to distribute available resources between a group of patients to achieve the best overall effect, typically the optimal balance between resource utilization and plan quality. This is achieved by taking the resource requirements into account already in the optimization of one or more treatment plans. For example, the method may be used to determine the best possible use of a limited resource such as a proton radiotherapy delivery system. In this case, the method may be used to optimize the distribution of resources to the different patients. In a preferred embodiment, the overall optimization according to the invention may be used to aim for the distribution of resources between the patients that will give the greatest benefit. In a further step, an individual treatment plan may be optimized for each patient given the resources allocated to this patient.

Another possible application of the invention is when different fractions delivered to a patient use different radiation sets, for example a first set having a higher number of beams and a second set having a reduced number of beams, to determine how many fractions should use the first set and how many should use the second set to achieve the best possible effect in a cost-efficient way.

In a preferred embodiment, the optimization problem further comprises at least one optimization function arranged to restrict the use of at least one of the first and the second set of resources. As is common in the art, each optimization function can be expressed as a constraint, defining a goal that must be fulfilled by the resulting plan, or a term in the objective function, that should be optimized to be as good as possible but which is traded against other terms in the objective. The optimization problem could include optimization functions related to all plans for all patients, the full plan for a single patient, to a subset of radiation sets, individual radiation sets or to individual beams within a radiation set. According to the invention, resources are considered for two or more radiation sets together.

The optimization problem preferably comprises an optimization function related to the target dose to be delivered by one of the radiation sets. The target dose may be set as the minimum, mean or median target dose, or the minimum dose that should be delivered to a specified fraction of the volume of the target.

In a preferred embodiment, the optimization problem further comprises at least one optimization function arranged to restrict the total delivery time over all radiation sets. Depending on the resources of the clinic, the available time slots for the different treatment machines can be considered already in the optimization when the delivery time or cost of the beam sets is included in the optimization.

The first radiation set may, for example, be a photon radiation set and the second radiation set may be an ion radiation set, such as a proton or carbon ion radiation set. Alternatively, the first and second radiation sets may be two different types of ion radiation sets, or any desired combination.

For joint optimization of plans for multiple patients, the optimization problem is preferably designed to jointly optimize plans for multiple patients by taking into consideration resource requirements and plan quality for multiple patients in the objective function and/or constraints.

A method according to any one of the preceding claims, wherein the optimization problem comprises at least one optimization function arranged to favour one of the radiation sets. This is suitably used where one of the radiation sets is more readily available than the other, to avoid overloading the less available radiation set.

The optimization problem may include functions which can favour different modalities regarding plan quality. Such functions could be related to plan robustness, either explicitly by using robust optimization functions, or implicitly by some surrogate for plan robustness, and/or dose outside the target, such as entrance dose, distal fall-off, and penumbra.

Models exist for predicting the positive or negative effect of switching from one plan to another. These models can be used to measure the effect of exchanging a fraction of a particular kind to another kind of fraction, that is, for example, with a high number of beams compared so using the reduced beam set, or with proton radiation compared to using photon radiation instead. Such models can be used to calculate the cost and benefit of including, for example, an additional fraction of proton radiation for a particular patient.

The cost according to the invention may be determined based on a number of different parameters, for example, one or more of the following:
actual monetary cost,
availability of equipment,
workload on available personnel, or
lost benefit to other patients who will not receive treatment.

The invention also relates to a computer program product comprising computer readable code means, preferably stored on a non-transitory storage medium, which, when run in a processor will cause the processor to perform the method according to any of the embodiments above.

A computer system comprising a processor, a data memory and a program memory, wherein the program memory comprises a computer program product according to the above, arranged to be run in the processor to control radiotherapy treatment planning.

BRIEF DESCRIPTION OF THE DRAWINGS

The invention will be described in more detail in the following, by way of example and with reference to the appended drawings, in which FIG. 1 is a flow chart of a first embodiment of a method that may be used according to the present invention FIG. 2 is a flow chart of a second embodiment of a method that may be used according to the present invention.

FIG. 3 is an overview of a computer system in which the methods according to the invention can be performed.

DETAILED DESCRIPTION

Generally, the optimization of treatment plans involves defining an optimization problem which may comprise one or more objective functions and one or more constraints. The objective functions define variables that should be optimized to be as good as possible. Constraints are absolute limits that may not be exceeded, for example a minimum dose to a target or a maximum dose to an organ at risk.

In the following, some examples will be discussed, for optimization using multiple radiation sets for a single patient and then for optimization using multiple radiation sets for more than one patient. The objective functions will be expressed in the examples in terms of "minimize" or "maximize" and the constraints will be presented as "subject to". In all of the examples below, the optimization problem may also comprise other objective terms and/or constraints than the ones listed, related to traditional optimization goals.

A solution to a multi-radiation set optimization with a resource requirement can be found in various ways: for example, the possible resource allocation may be discretized, and a solution may be calculated for each alternative. This process may be repeated a number of times to gradually improve the resolution of the discretization. Another method would be to disregard the resource requirement during the optimization and then round the optimized solution to a feasible point, for example, by rounding to a nearest integer number of fractions. The optimization could then continue, taking the resource requirements into account. It would also be possible to let the resources be represented as variables in the optimization.

The optimization problem may comprise an objective function optimizing the result for the patient with constraints on the availability of resources, or vice versa an objective function optimizing the use of resources with constraints on the minimum acceptable quality of the treatment given to the patient.

For optimizing a treatment using multiple radiation sets having different treatment techniques for a single patient, it is often the case that one treatment technique is preferred but also less available.

One type of constraint that may be used is a maximum total time $t^{max}$ for the treatment. For a plan using VMAT and SMLC radiation sets a possible optimization problem with such a constraint becomes $$\text{minimize } f(d_{SMLC}, d_{VMAT}) \quad (1)$$

$$\text{subject to } t_{SMLC} + t_{VMAT} \leq t^{max},$$

where $f(d_{SMLC}, d_{VMAT})$ is an objective function related to the dose distribution $d_{SMLC}$ of the SMLC radiation set and the dose distribution $d_{VMAT}$ of the VMAT radiation set, and where $t_{SMLC}$ and $t_{VMAT}$ are the delivery times of the SMLC radiation set and the VMAT radiation set, respectively. The objective function could for example score the individual doses of the radiation sets, or score the summed dose of the radiation sets, or a combination thereof, that is:

$$f(d_{SMLC}, d_{VMAT}) = f_1(d_{SMLC}) + f_2(d_{VMAT}) + f_3(d_{SMLC} + d_{VMAT}) \quad (2)$$

for some objective constituent functions $f_1$, $f_2$, and $f_3$. In addition, a constraint may be set on the maximum time $t^{max}_{SMLC}$ spent on the SMLC radiation set, the maximum time $t^{max}_{VMAT}$ spent on the VMAT radiation set, or on each of the radiation sets individually, that is:

$$t_{SMLC} \leq t^{max}_{SMLC} \text{ and } t_{VMAT} \leq t^{max}_{VMAT} \quad (3)$$

Another situation when one treatment technique is preferred but also less available may arise if quality assurance (QA) is taken into consideration. Patient-specific QA is often a limited resource as it involves the delivery of the planned treatment on a phantom geometry and measurement and analysis of the delivered dose. For some, complex, treatment techniques, such as SMLC or VMAT, QA is often considered necessary, and typically requires special resources. For simpler treatment techniques, such as 3D-CRT, QA may not be needed, or if it is performed, will be less costly. Complex techniques also involve a higher risk that the QA fails, so that a new plan must be optimized. Therefore, the advantages of a treatment technique that requires patient-specific QA must be weighed against the cost for QA in terms of workload and treatment machine usage. An example of an optimization formulation that incorporates such a trade-off is simultaneous optimization of three-dimensional conformal radiotherapy (3DCRT) and SMLC radiation sets according to $$\text{minimize } f(d_{SMLC}, d_{3DCRT}) + g(x_{SMLC}, x_{3DCRT}) \quad (4)$$

where $x_{3DCRT}$ and $x_{SMLC}$ are the optimization variables for the 3DCRT and SMLC radiation set, respectively, where $d_{3DCRT}$ and $d_{SMLC}$ is the dose distribution for respectively the 3DCRT and SMLC radiation set, and the function g is a function that quantifies the cost of the resources necessary for QA of the 3DCRT and SMLC radiation sets given the current configuration of the optimization variables.

In a related application, the risk for a plan failing the QA assessment and thereby mandating re-planning is incorporated in the optimization. In such applications, simultaneous optimization of 3DCRT and SMLC radiation sets where the risk for QA failure is constrained to be within some threshold level b may be formulated according to $$\text{minimize } f(d_{SMLC}, d_{3DCRT}) \quad (5)$$

$$\text{subject to } p(x_{SMLC}, x_{3DCRT}) \leq b.$$

where p is a function that predicts the gamma analysis passing rate and calculates an estimate of how likely the combined 3DCRT and SMLC treatment is to fail the QA assessment. Such an optimization function may be based on a prediction model constructed by machine learning applied to historic treatment plans.

If a combination of treatment techniques is used, a constraint could be added on the number of fractions that should use one modality, or each of the modalities. This could be suitable in situations in which there are regulations on how much a particular technique can be used for the type of patient under consideration. For example, a treatment, which is to be delivered in a total of $n_f$ fractions, combining photon and carbon radiotherapy may be subject to a constraint that at most a certain number $n_c$ of carbon fractions can be used, while the number $n_{ph}$ of photon fractions is constrained to equal $n_f - n_c$, i.e., $n_{ph} + n_c = n_f$. In this case, the optimization problem may be set up as follows:

$$\text{minimize } f(d_{ph}, d_c) \quad (6)$$

subject to $$n_c = (\text{mean target dose carbon})/(\text{fraction size carbon})$$

$$n_c \leq (\text{max number of carbon fractions})$$

$$n_{ph} = (\text{mean target dose photons})/(\text{fraction size photons})$$

$$n_{ph} + n_c = n_f$$

The numbers of carbon fractions $n_c$ and photon fractions $n_{ph}$ respectively are variables in this optimization problem, and can be used in the objective function as well, for example to impose penalties on doses to organs that are sensitive to radiation dependent on the number of fractions. An example of such a function would be $$\sum_{i \in OAR} \max(d_{ph,i} - n_{ph} d_{ph,i}^{ref}, 0)^2 \quad (7)$$

where $d_{ph,i}^{ref}$ is the maximally allowed fraction photon dose for the organ. That is, for each voxel i in the set OAR of voxels of the sensitive organ, there is a quadratic penalty if the total dose is greater than the maximally allowed fraction dose times the number of fractions.

A combination of equations (1), (3) and (6) may be used in the optimization problem, that is, both a constraint on the time per fraction and a constraint on the number of fractions.

If two modalities using different types of ions are combined, the use of each type of ion may be optimized with limits on how much each modality can be used.

As mentioned above, a common combination of treatment modalities is photon therapy and proton therapy. Proton therapy delivery systems are less common than photon delivery systems, and are therefore a limited resource. At the same time, proton therapy is advantageous and preferable over photon therapy in many cases. One solution is to give patients a number of proton fractions and the remaining fractions as photon therapy. The optimal number of proton fractions is the number where the last one still gives a certain degree of improvement.

To achieve this, the optimization may be subject to a constraint that for an additional proton fraction to be given, it must improve some measure of quality by at least a minimum amount. A suitable measure of quality to apply in this case is normal tissue complication probability (NTCP). This may be achieved in different ways, as will be discussed in the following.

For example, different partitioning s of photon and proton fractions may be solved explicitly, that is, different combinations of numbers of photon and proton fractions, respectively. In the general case, this involves starting with an initial number of fractions to be used for each radiation set, the sum of initial numbers of fractions being the total number of fractions in the treatment. The radiation set optimization for all radiation sets together is performed and the quality measure is evaluated. Next, the initial numbers of fractions are changed, but the sum still being the total number of fractions, and a new optimization is performed and the quality measure is evaluated. This is repeated a number of times for different combinations of the number of fractions of each of the radiation sets until a satisfactory quality measure is achieved. The combination of number of fractions for each of the radiation sets that gives the most satisfactory result is selected.

FIG. 1 is a flow chart of an embodiment of a sequential method to determine the optimal number of proton fractions and photon fractions respectively, in a dual radiation set. In step S11, a first number $n_{pr}$ of proton fractions is set, typically 0, and a first number $n_{ph}$ of photon fractions is set. The sum of $n_{pr}$ and $n_{pf}$ should always be equal to the total number of fractions $n_f$.

In step S12, an optimization is performed on both radiation sets together, that is, in this example, proton and photon radiation sets. In step S13 a quality measure is evaluated.

In step S14 it is determined, based on the quality measure, if another set of fraction numbers should be evaluated. If yes, continue with step S15 to form a new loop, if no, the procedure ends. In step S15 the number $n_{pr}$ of proton fractions is incremented by an integer number, for example by one. Also, the number $n_{ph}$ of photon fractions is decremented by the same integer number. The procedure then returns to step S12.

In step S14, typically, the procedure continues with a new loop if the latest quality measure is improved compared to the previous quality measure. A threshold may be set so that if the quality measure does not improve by more than a certain value the process will end. Alternatively, a target value may be set for the quality measure and when the quality measure reaches that target value the procedure ends.

This method is based on the insight that an increased number of proton fractions will typically improve the plan quality, while photon therapy is less expensive and more easily available. In general, therefore, the number of fractions of the most limited resource should start at 0, or at a low number to be incremented by a certain amount between each optimization, and the more available resource should start at the total number of fractions, or at a high number to be decremented by the same amount. When a further increase in the number of proton fractions no longer results in a significant improvement of the quality measure, the process should stop and the current values for $n_{pr}$ and $n_{ph}$ should be used in plan optimization, as indicated in step S16.

FIG. 2 shows an alternative embodiment involving a binary search method to determine the optimal number of proton fractions and photon fractions respectively, in a dual radiation optimization starting in step S21 with an extreme partitioning of the fractions, e.g., $n_{pr}=0$ proton fractions and $n_{ph}=n_f$ photon fractions. In step S21, two additional variables, L and R, corresponding to lower and upper bounds for the number of proton fractions during the binary search, are introduced. In step S22, the plan quality is calculated for $n_{pr}$ and $n_{ph}$, and for $n_{pr}+1$ and $n_{ph}-1$, respectively. In step S23, the difference in quality between the two calculations performed in step S22 is determined, which will typically indicate that the higher number of proton fractions involves an improvement over the lower number.

In step S24, it is determined if another optimization should be performed. If no, the procedure ends. If yes, in step S25, a new set of fraction numbers is determined, based on the magnitude of the improvement determined in step S23, for example in the following way: If the improvement is above a limit, L is set to the current value of $n_{pr}$, and then $n_{pr}$ is increased to a point between L and R for example the midpoint between them, rounded if the number is not integer. If the number is below the limit, R is set to the current value of $n_{pr}$ and then $n_{pr}$ is decreased to a point between L and R, for example the midpoint between them, rounded if the number is not integer. The number of photon fractions $n_{ph}$ is set so that $n_{pr}+n_{ph}=n_f$. If no, the procedure ends and the current fraction numbers $n_{pr}$ and $n_{ph}$ are used in plan optimization, as indicated by step S26.

In step S24 the determination step may advantageously be based on the size of the interval [L, R]. When the size of the interval is below a certain value, the procedure ends.

The problem could also be solved approximately, by scaling a predetermined photon plan and a predetermined proton plan according to different partitionings of fractions, and selecting the number based on the resulting, approximate, quality increase. When the partitioning has been determined, a multiple beam set optimization with the determined resource limit could be performed to further improve the plan quality.

Even if two treatment modalities are used that are more equal in quality so that one is not generally preferable over the other, it may still be feasible to optimize on a combination of radiation sets, to utilize the fact that they have different properties. For example, one modality may be less affected by uncertainties such as patient setup uncertainty, whereas the other provides sharper dose gradients, thereby enabling more precise treatment.

In the following, some examples of how optimization problems may be set up for multiple patients with multiple radiation sets will be discussed.

It would be possible to set up a complete optimization problem for all patients as a combination of all the patients' optimization problems with additional objective functions or constraints related to the overall use of resources and solve the whole optimization problem in one operation. The overall use of resources can be taken into account in the form of total resource availability, benefits for each patient's specific situation and the quality measures as discussed above.

A simpler overall optimization problem may be used to determine the optimal distribution of resources between patients, for example in the sense that one patient may benefit more from an additional proton fraction than another patient. In that case, the actual treatment plan for each patient could be calculated afterwards, using the combination of modalities allocated to that patient. A constraint may be that for one particular radiation set, with limited resources, only a certain number of fractions are available in a given time period. The optimization problem should be set up so that these fractions are distributed in the optimal way among the patients that will benefit the most from this radiation set.

As mentioned above, a combination of photon and proton fractions are often used, with proton fractions being generally better but also more costly and more scarce. To determine the best way to distribute a limited number of proton fractions between two or more patients, one could optimize the plans for the patients simultaneously using an optimization problem such as the following, where n is the number of patients and, for patient i, $f_i$ is the objective function, $d_{pr}^{(i)}$ is the proton dose, $d_{pr}^{(i)}$ is the photon dose, $n_{pr,i}$ is the number of proton fractions, (mean target proton dose)$_i$ is the mean target proton dose and (fraction size)$_i$ is the fraction size:

$$\text{minimize } \Sigma_{i=1}^{n} f_i(d_{pr}^{(i)}, d_{ph}^{(i)}) \quad (8)$$

subject to $n_{pr,i}$=(mean target proton dose)$_i$/(fraction size)$_i$ for $i=1,\ldots,n$ $\Sigma_{i=1}^{n} n_{pr,i} \leq$ (max no of proton fractions)

Similar problems could be set up for any machine, modality, operator, etc., representing a limited resource. The constraint may be expressed in terms of number of fractions, fraction size and/or the amount of time the machine is available.

Even if there are no bounds on the available resources, it may still be advantageous to optimize the best way of distributing resources, if the optimal combination of resources is non-trivial. For example, in simultaneous optimization of protons and photons, it may not be optimal to only use proton fractions if robustness against geometric errors are taken into account, since protons are generally more affected by geometric errors. In that case, an optimization problem similar to Eq. (6), but with "protons" substituted for "carbon", can be used, with a user-defined upper limit on the number of proton fractions. As another example, the optimal combination of ion species taking relative biological effectiveness and geometric uncertainties into account is far from trivial.

FIG. 3 is a schematic representation of a computer system in which the inventive method may be performed. A computer 31 comprises a processor 33, a first and a second data memory 34, 35 and a program memory 36. Preferably, one or more user input means 38, 39 are also present, in the form of a keyboard, a mouse, a joystick, voice recognition means or any other available user input means. The user input means may also be arranged to receive data from an external memory unit.

The first data memory 34 comprises necessary data for performing the method, including values for $n_f$, $n_{pr}$, $n_{ph}$ and applicable thresholds and limits. The second data memory 35 holds data related to one or more current patients for which treatment plans are to be developed. The first program memory holds a computer program arranged to make the computer perform the method steps, for example, as discussed in connection with FIG. 1 or FIG. 2.

As will be understood, the data memories 34, 35 as well as the program memory 36 are shown and discussed schematically. There may be several data memory units, each holding one or more different types of data, or one data memory holding all data in a suitably structured way, and the same holds for the program memories.

The invention claimed is:

1. A computer-based method of optimization of at least one treatment plan involving at least a first and a second radiation set, where the first radiation set is to be delivered to a first patient and the second radiation set is to be delivered to the first patient or to a second patient, the first and second radiation set requiring a first and a second set of resources, respectively, wherein the optimization is performed using an optimization problem comprising an optimization function related to the first and second sets of resources, wherein the optimization problem is designed to optimize the allocation of resources between at least two patients.

2. The method according to claim 1, wherein the optimization problem further comprises at least one optimization function arranged to restrict the use of at least one of the first and the second set of resources.

3. The method according to claim 1, wherein the optimization problem comprises an optimization function related to the target dose to be delivered by one of the radiation sets.

4. The method according to claim 1, wherein the optimization problem further comprises at least one optimization function arranged to restrict the total delivery time over all radiation sets.

5. The method according to claim 1, wherein the first radiation set is a photon radiation set and the second radiation set is an ion radiation set, such as a proton or carbon radiation set.

6. The method according to claim 1, wherein the at least one treatment plan involves delivering the first and the second radiation set as a number of fractions, and the optimization problem is designed to determine the number of fractions to be included in the plan for each of the radiation sets.

7. The method according to claim 6, comprising the step of determining the number of fractions of the first radiation set to be included in the at least one treatment plan based on the resulting plan quality achieved with said number of fractions, using a suitable measure of quality, such as normal tissue complication probability, NTCP.

8. The method according to claim 1, wherein the optimization problem is designed to jointly optimize plans for multiple patients by taking into consideration resource requirements and plan quality for multiple patients in the objective function and/or constraints.

9. The method according to claim 1, wherein the optimization problem comprises at least one optimization function arranged to favour one of the radiation sets.

10. A computer program product comprising computer readable code means, stored on a non-transitory storage medium, which, when run in a processor will cause the processor to perform the method according to claim 1.

11. A computer system comprising a processor, at least one data memory and a program memory, wherein the program memory comprises a computer program product according to claim 10 arranged to be run in the processor to control radiotherapy treatment planning.

* * * * *